United States Patent [19]
Patel et al.

[11] Patent Number: 5,736,026
[45] Date of Patent: Apr. 7, 1998

[54] BIOMASS-FUEL CELL COGENERATION APPARATUS AND METHOD

[75] Inventors: Pinakin S. Patel; Jen Jung Fan, both of Danbury, Conn.

[73] Assignee: Energy Research Corporation, Danbury, Conn.

[21] Appl. No.: 596,616

[22] Filed: Feb. 5, 1996

[51] Int. Cl.⁶ .................................................. C25B 1/00
[52] U.S. Cl. ................... 205/343; 429/2; 429/17; 429/19
[58] Field of Search .................... 429/2, 17, 19; 205/343

[56] References Cited

U.S. PATENT DOCUMENTS

| | | | |
|---|---|---|---|
| 5,500,306 | 3/1996 | Hsu et al. | 429/17 |
| 5,554,453 | 9/1996 | Steinfeld et al. | 429/17 |

*Primary Examiner*—Bruce F. Bell
*Attorney, Agent, or Firm*—Robin, Blecker, Daley and Driscoll

[57] ABSTRACT

Integrated ethanol manufacturing by fermentation of biomass, with an electrical fuel cell generator of electrical and heat energy, the cogeneration including use by the fuel cell of the alcohol, and of the carbon dioxide from the fermentation, which increases the generation of energy, and use by the alcohol manufacturing of the heat and electrical energy from the fuel cell, which increases the fuel manufacture.

46 Claims, 10 Drawing Sheets

BIOMASS-FUEL CELL COGENERATION APPARATUS AND METHOD

BACKGROUND OF THE INVENTION

1. Field of the Invention

This invention pertains to intimate integration of a fuel cell, mechanically, chemically, and electrically with a microorganism using process which synthesizes ethyl alcohol from agricultural material or from waste. It includes cooperation of an electrical generator fuel cell with at least one stage to nearly all stages of ethanol manufacture, from the stage of mashing a starting material such as corn, through fermentation, to production of alcohol, electricity and heat energy.

2. Description of the Prior Art

Presently alcohol (ethanol) is synthesized for production purposes by fermentation of a biomass, preferably an agricultural product such as corn. The alcohol is usually manufactured to a concentrated or "fully dewatered" state of at least 199+ proof, that is, dewatered better than 99.5% by volume, for use such as a fuel additive to gasoline.

Alcohol manufacture is extremely energy-intensive and costly, especially if processed to 199 proof. Electrical and heat energy needed for the manufacture is costly in terms of dollars and pollution caused by its generation. The energy is obtained by purchasing electricity from a distant utility company, or by burning gasoline, coal, or oil in gas or diesel generators and steam boiler on-site installations. In some installations, a portion of the alcohol is burned to supplement the gasoline or oil, but for this the alcohol must be fully dewatered.

SUMMARY OF THE INVENTION

The present invention ameliorates those factors which contribute to high cost, low efficiency and pollution in the manufacture of alcohol.

It is one object of the invention to provide low cost, virtually pollution free electrical energy and heat energy manufactured on the alcohol production site.

It is another object of the invention to generate the on-site electrical energy and heat energy from fuel derived from the alcohol and from non-combustible by products of the on-site alcohol manufacturing.

It is another object of the invention to provide the above electrical energy and heat energy for use in the alcohol manufacturing.

It is another object that the generator of the on-site electrical energy and heat energy can be fueled from partially dewatered alcohol from the on-site alcohol manufacturing.

It is another object that the generator of the on-site electrical energy and heat energy can be fueled with carbon dioxide from the on-site alcohol manufacturing.

Other objects and advantages will become obvious to one reading the ensuing description of the present invention.

Means for holding a biomass is attached to means for fermenting the biomass. Means for separating alcohol from the fermented biomass is connected to the means for fermenting and to an electrical fuel cell for receiving of the alcohol and for generating of electrical energy electrochemically and of chemical heat energy by the fuel cell. Means for transferring the chemical heat energy generated by the fuel cell is connected to means for holding the biomass such as in distillation means for separating alcohol from the fermented biomass, in means for cooking the biomass, and in means for drying the biomass. Means for reducing thebiomass to smaller parts is connected to the electrical fuel cell for being operated by energy from the fuel cell. The fuel cell is also connected to the fermentation process for using carbon dioxide from the fermentation process in the generation of electrical and heat energy. In one arrangement, reformer means is connected to the means for separating and to the fuel cell for reforming the alcohol to hydrogen for the receiving of the alcohol by the fuel cell. In another arrangement, conversion means is connected to the means for separating and the fuel cell for converting the alcohol to methane for the receiving of the alcohol by the fuel cell.

BRIEF DESCRIPTION OF THE DRAWINGS

In order that the invention be more fully comprehended, it will now be described, by way of example, with reference to the accompanying drawings, in which.

DESCRIPTION OF THE PREFERRED EMBODIMENTS

Before explaining the invention in detail, it is to be understood that the invention is not limited in its application to the detail of construction and arrangement of parts illustrated in the drawings since the invention is capable of other embodiments and of being practiced or carried out in various ways. It is also to be understood that the phraseology or terminology employed is for the purpose of description only-and not of limitation.

Figure 1:
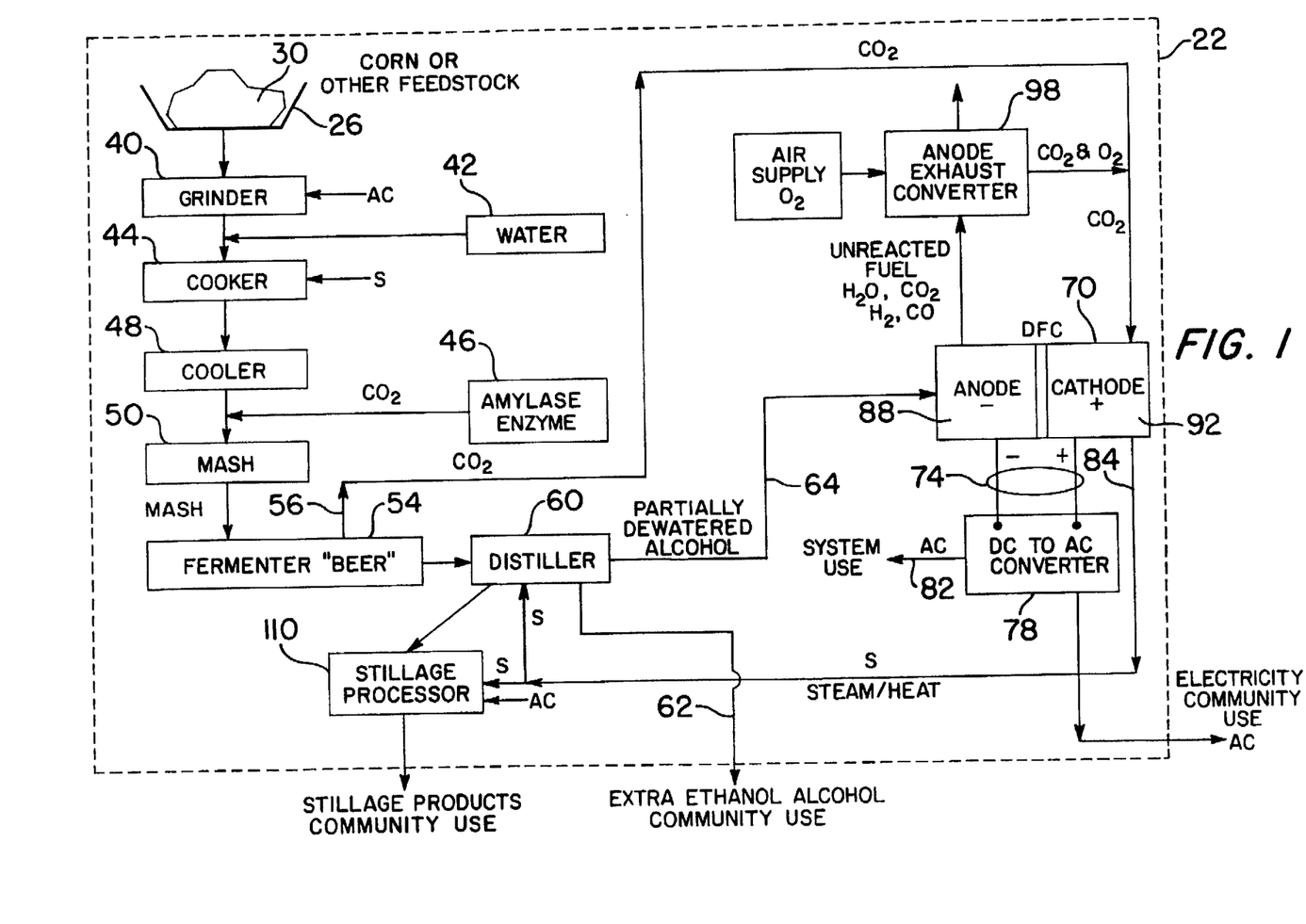
FIG. 1 is a schematic diagram of a cogeneration system according to the present invention.

Referring to FIG. 1, biomass fermentation-electrical fuel cell cogeneration system 22 is designed to operate with various biomass items including sugar crops such as sugar beets, sweet sorghum, sugar cane; starch crops including grains such as corn, wheat, and barley, and tubers such as potatoes; and with other fermentable feedstocks. The system is also designed to serve alcohol production sites from 0.5 million gallons per year individual farm, to 100 million gallon per year in size, which may produce one or a combination of end products of alcohol (ethanol) in various concentrations, animal feed, electrical energy for community (outside the system) use, and heat energy for community use.

For purpose of description, the feedstock is corn. The site is a farm of 100 to 500 acres, and the products are alcohol, animal feed, and electrical energy for community use. System 22 also manufactures all the energy needed for operation of the system.

Biomass delivery module 26 delivers corn 30 to means to break the biomass into smaller parts such as in wet or dry milling, herein called grinder 40. The ground corn is cooked with water 42 in cooker 44, and cooled in cooler 48. An amylase enzyme 46 is added to accelerate hydrolysis, and the resulting mash 50, which undergoes sacharification to provide simple soluble fermentable sugars, is provided to fermenter 54.

The fermentation process produces alcohol up to about 9 wt. percent concentration at which percent level microbial fermentation activity is hindered by pollution of the fermenting mash by the alcohol. The fermentation process also produces carbon dioxide 56.

The fermenting mash, often called "beer", is distilled in distiller 60 to provide alcohol at various desired levels of concentration. Distillation may be by heat, heat and vacuum, or other known means, and may be supplemented with azeotropic separation such as by a molecular sieve.

Preferably, fully dewatered alcohol 62 is provided for community use, and partially dewatered alcohol 64 is provided for fueling electrical fuel cell 70.

By the term "partially dewatered alcohol" it is meant ethyl alcohol produced by fermentation wherein beer alcohol is distilled or purified to less than 99% concentration by volume, and it excludes fully dewatered ethyl alcohol of 99% or better including fully dewatered ethyl alcohol to which water has been added.

Electrical fuel cell 70 generates electricity electrochemically in the form of direct current which is delivered by electrical lines 74 to converter 78 which preferably inverts the direct current to alternating 82 (AC) at commercial 60 cycles, 220 volts AC for use in system 22, and 60 cycle 110 volts for community use.

Electrical fuel cell 70 also generates chemical heat energy, as an air/steam mixture (S) at about 1,300 degrees Fahrenheit, from the cathode 92 side of the fuel cell.

Electrical fuel cell 70 is preferably a self reforming fuel cell, preferably having a molten carbonate electrolyte, and preferably one that reforms alcohol and other fuels such as methane and diesel at anode 88 to form hydrogen for use in the cell. This internally reforming fuel cell, often called a "direct" fuel cell, usually requires water supplied to the anode with most fuels, and, depending upon the fuel, provides excess hydrogen and carbon monoxide from the anode. If a molten carbonate electrolyte is used, it may be called an internally reforming molten carbonate fuel cell, or IRMCFC.

For purpose of description herein, the internally reforming fuel cell will be called a direct fuel cell or DFC. A carbonate fuel cell which does not reform internally will be called a carbonate fuel cell or CFC.

The requirement for water at the reforming anode contributes significantly to the efficiency advantage of system 22 over present alcohol production systems. This is because electrical and heat energy provided by the system, for community use for example, may be generated from partially dewatered alcohol at, for example, 30% alcohol by volume. This eliminates much of the energy and capital equipment presently applied to fully dewater the alcohol for fueling present combustion electrical and heat energy generation systems.

Figure 2:
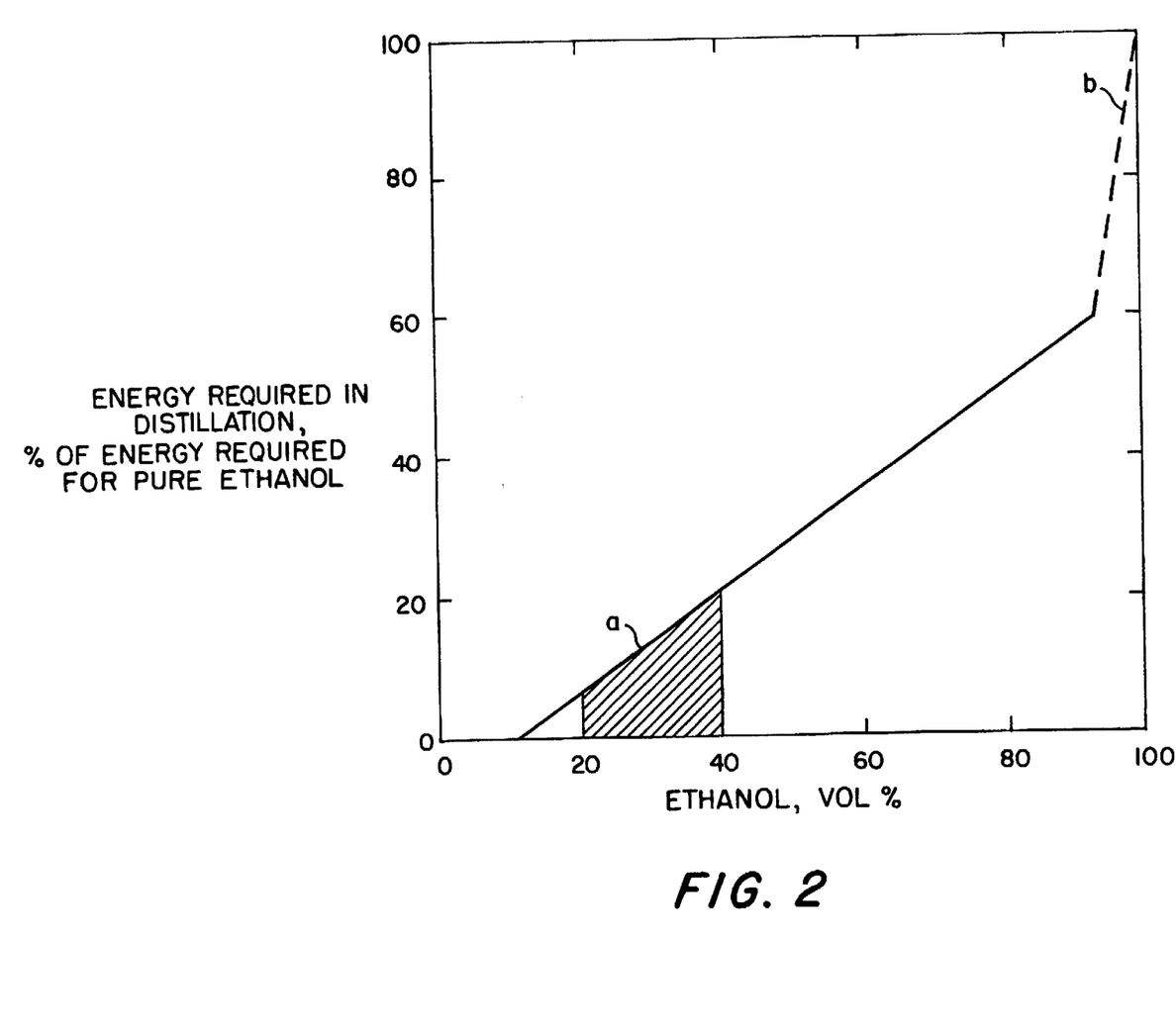
FIG. 2 is a graph showing energy requirements for alcohol purification.

FIG. 2 shows that energy (a) required in distilling beer to the preferred range for use in a cogeneration system of the present invention is small compared to energy (b) used to purify ethanol to fully dewatered concentration for use in combustion electrical and heat energy generation systems.

Fully dewatered alcohol is free from impurities. Partially dewatered alcohol may include such impurities as maltose, saccharides, glycerol, methanol, dextrose, sulfur and insoluble material. For example, at 9 wt %, dewatered state, the ethanol will typically include water 90 wt %, high molecular weight organics 1.0–3.0%, sulfur 0.1–0.22%, insoluble material somewhat less than 0.2%, and inorganics somewhat less than 1.0%. The impurities, however, drop to negligible levels at 50% by volume dewater. Furthermore, the higher hydrocarbons can be handled by the DFC, filtration removes insolubles, and sulfur which is used with wet milling of the biomass is not a factor in dry milling.

Equations (1) through (4) show the operation of a fuel cell fueled with partially dewatered alcohol. For simplicity of description, the impurities in dewatered alcohol are ignored.

Reforming Of the alcohol to hydrogen takes place internally in the anode compartment of the DFC:

$$C_2H_5OH + 3H_2O \rightarrow 6H_2 + 2CO_2 \text{ (endothermic)} \quad (1)$$

The hydrogen is used by the cell.
At the anode:

$$H_2 + CO_3^- \rightarrow H_2O + CO_2 + 2e^- \quad (2)$$

At the cathode:

$$CO_2 + \tfrac{1}{2}O_2 + 2e^- \rightarrow CO_3^- \text{ (which arrives at the node)} \quad (3)$$

Overall:

$$H_2 + \tfrac{1}{2}O_2 \rightarrow H_2O \text{ (exothermic)} + \text{electricity} \quad (4)$$

Comparing the above equations with FIG. 1, it may be seen that an increase in chemical activity increases electrical energy and chemical heat energy output of the fuel cell. Increasing the alcohol to anode 88 provides for increased chemical activity. Increasing the carbon dioxide to cathode 92 also provides for increased chemical activity.

Anode exhaust converter 98 processes unreacted fuel to supply $CO_2$ required for the cathode reaction. The converter can be a physical, chemical or electromechanical separator. An anode exhaust converter is described, for example, in U.S. Pat. No. 4,791,033, patented Dec. 13, 1988 by P. Patel.

Carbon dioxide 56, provided directly from fermenter 54, further boosts the electrical and heat energy output of system 22.

The above features of system 22 provide benefits for a community surrounding an alcohol manufacturing site, and efficiencies in the generation of electrical and heat energy in alcohol production-site power generation systems, heretofore not provided.

Figure 3:
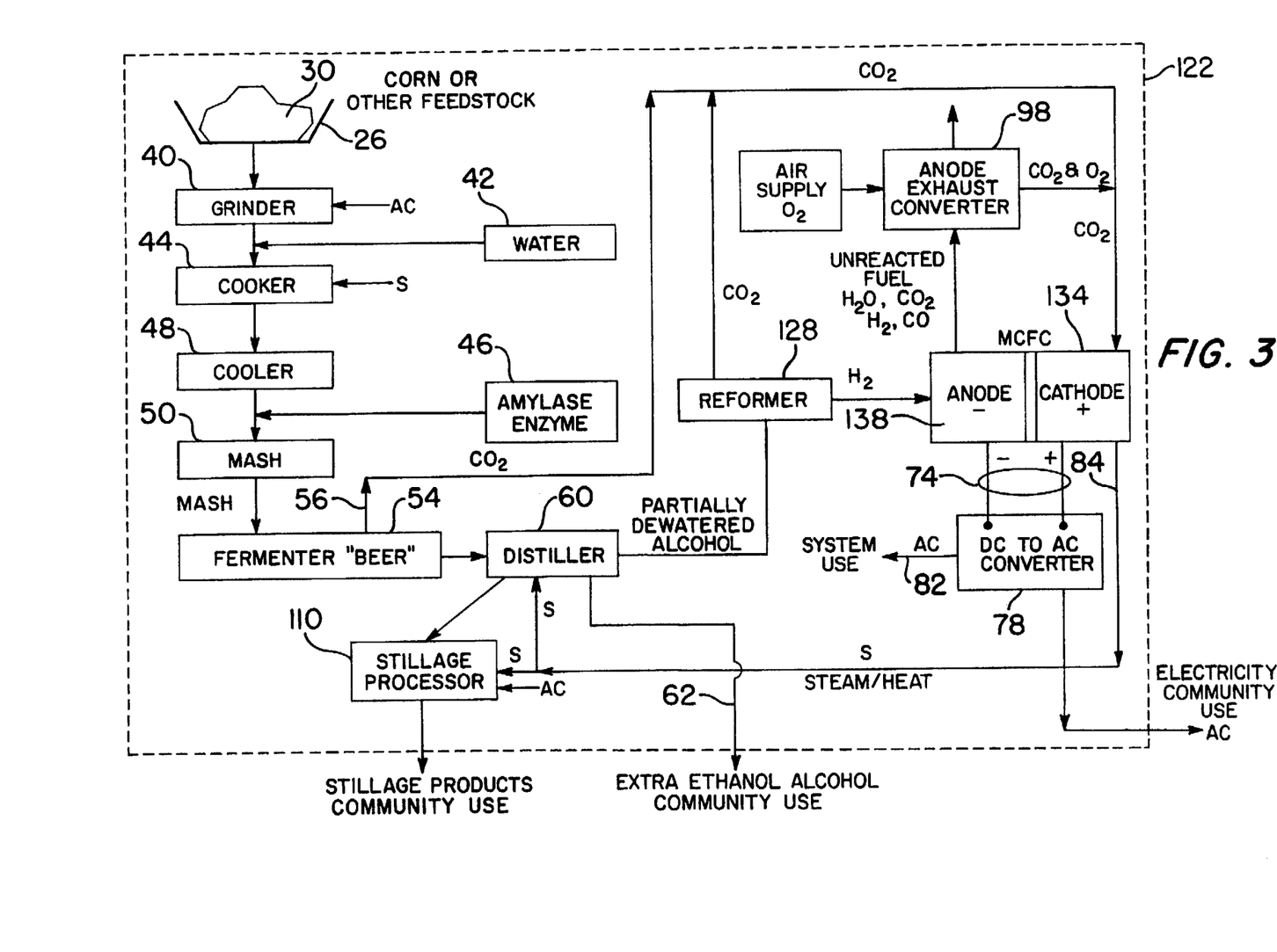
FIG. 3 is a schematic diagram of a cogeneration system according to the present invention.
Figure 4:
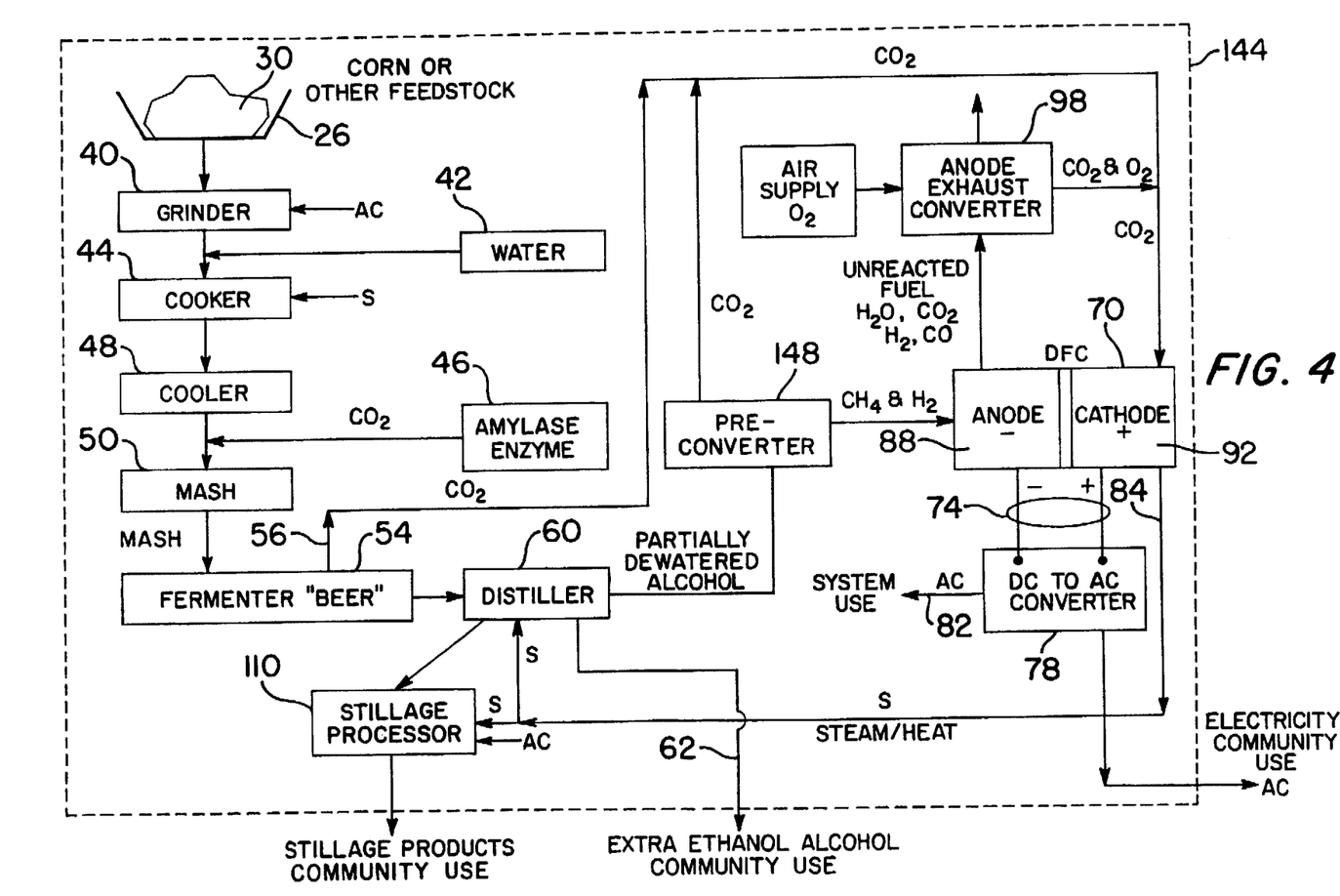
FIG. 4 is a schematic diagram of a cogeneration system according to the present invention.

Further efficiency in system 22 is provided by transferring heat energy 84 from cathode 92 directly to cooker 44. Thermal energy available from the cathode at about 1,300 degrees Fahrenheit as shown in FIGS. 1, 3 and 4 can be piped directly or indirectly to the cooker which uses the air/steam to raise the temperature of the mixture and for jet cooking in which steam at 125 to 150 psig. is injected into the mash in the cooker.

Further increased efficiency is obtained by transferring heat energy from the cathode to distiller 60, which in turn causes the alcohol to be driven from the beer in various concentrations desired for further fueling the anode 88, and for providing alcohol for community use.

In similar manner, grinder 40, which receives electrical energy 82 from DC to AC converter 78, contributes to manufacture of the alcohol, the provision to fuel cell 70 anode 88 of the alcohol fuel, and the provision of carbon dioxide for cathode 92. This in turn provides more electrical energy for the grinder as well as for the rest of system 22 and the community.

Heat energy from anode exhaust converter 98 is used to preheat the air+$CO_2$ for the fuel cell cathode to the cathode's operating temperature. It may also be provided as needed to the cooker, distiller and to stillage processor 110.

Stillage processor 110 may also receive heat energy 84 from cathode 92, and receives electrical energy 82 from converter 78. The stillage may be dried and packaged for shipping as high protein animal food. On a self-supporting alcohol manufacturing cogeneration site, however, it may be minimally processed and provided in the wet form for farm animal feed in the community immediate to cogeneration system 22.

Experiment with a DFC using dilute ethanol and partially dewatered alcohol obtained directly from commercial ethanol plants indicated that the DFC will operate with an alcohol concentration of 1% to 60% by volume. The preferred percentage being between 15%–30%.

Carbon formation at the anode of the fuel cell becomes a concern at concentrations above 35%.

Experimental results show that carbon deposition occurs at steam to carbon ratio of 4.5 or lower.

The steam to carbon ratio is determined by the relative concentrations of water and ethanol. A high steam to carbon ratio is obtained with partially dewatered alcohol of low alcohol concentration, for example a ratio of 15.0 for ethanol at 10% by volume such as would be obtained from the fermenter. The steam to carbon ratio decreases as the ethanol concentration increases, such as a ratio of 3.5 with 31.7% ethanol by volume.

Although increasing the steam to carbon ratio reduces the likelihood of carbon deposition, it may also reduce fuel cell electrical energy output.

Referring to FIG. 3, biomass fermentation-electrical fuel cell cogeneration system 122 includes reformer 128 which converts partially dewatered alcohol to carbon dioxide and hydrogen, as shown in the following equation (5).

$$C_2H_5OH + 3H_2O \rightarrow 6H_2 + 2CO_2 \text{ (endothermic)} \quad (5)$$

CFC fuel cell 134 includes reformer 128 which is external to anode 138, for receiving of alcohol and generating of electricity by the fuel cell.

Fuel cell 134 preferably has a molten carbonate electrolyte and operates as in the following equations (6) through (8).
At the anode:

$$H_2 + CO_3^{=} \rightarrow H_2O + CO_2 + 2e^{-} \quad (6)$$

At the cathode:

$$CO_2 + \tfrac{1}{2}O_2 + 2e^{-} \rightarrow CO_3^{=} \text{(which arrives at the anode)} \quad (7)$$

Overall:

$$H_2 + \tfrac{1}{2}O_2 \rightarrow H_2O \text{ (exothermic)+electricity} \quad (8)$$

The efficiency advantages provided by system 122 are similar to those of system 22. Equations (6) through (8) show system 122 operating with a carbonate fuel cell for fuel cell 134. A DFC will also work well for fuel cell 134 in this arrangement and provides even better efficiency because of better thermal management.

A DFC was test run with and without a preconverter and with different steam to carbon ratios.

In general, a preconverter is a low-temperature, adiabatic reformer. Partially dewatered alcohol is reformed to generate methane and carbon dioxide. The preconverted ethanol is then fed to the internally reforming fuel cell.

With a preconverter you can operate with lower steam to carbon ratios to provide higher fuel cell output because the preconverter can convert the higher hydrocarbons which would otherwise contribute to harmful carbon formation at the lower steam to carbon ratios.

In FIG. 4, biomass fermentation-electrical fuel cell cogeneration system 144 includes preconverter 148 which converts partially dewatered alcohol to methane. A formula for this conversion is formula (9).

$$C_2H_5OH + H_2O \xrightarrow{[catalyst]} CH_4 + CO_2 + 2H_2 \quad (9)$$

The methane rich fuel is processed in DFC 70 according to the following equations (10) through (13).
At the anode compartment:

$$CH_4 + H_2O \text{ (added)} \rightarrow CO + 3H_2 \text{ (endothermic)} \quad (10)$$

At the anode:

$$H_2 + CO_3^{=} \rightarrow H_2O + CO_2 + 2e^{-} \quad (11)$$

At the cathode:

$$CO_2 + \tfrac{1}{2}O_2 + 2e^{-} \rightarrow CO_3^{=} \text{(which arrives at the anode)} \quad (12)$$

Overall:

$$H_2 + \tfrac{1}{2}O_2 \rightarrow H_2O \text{ (exothermic)+electricity} \quad (13)$$

The efficiency advantages provided by system 144 are similar to or better than those of system 22.

Figure 5:
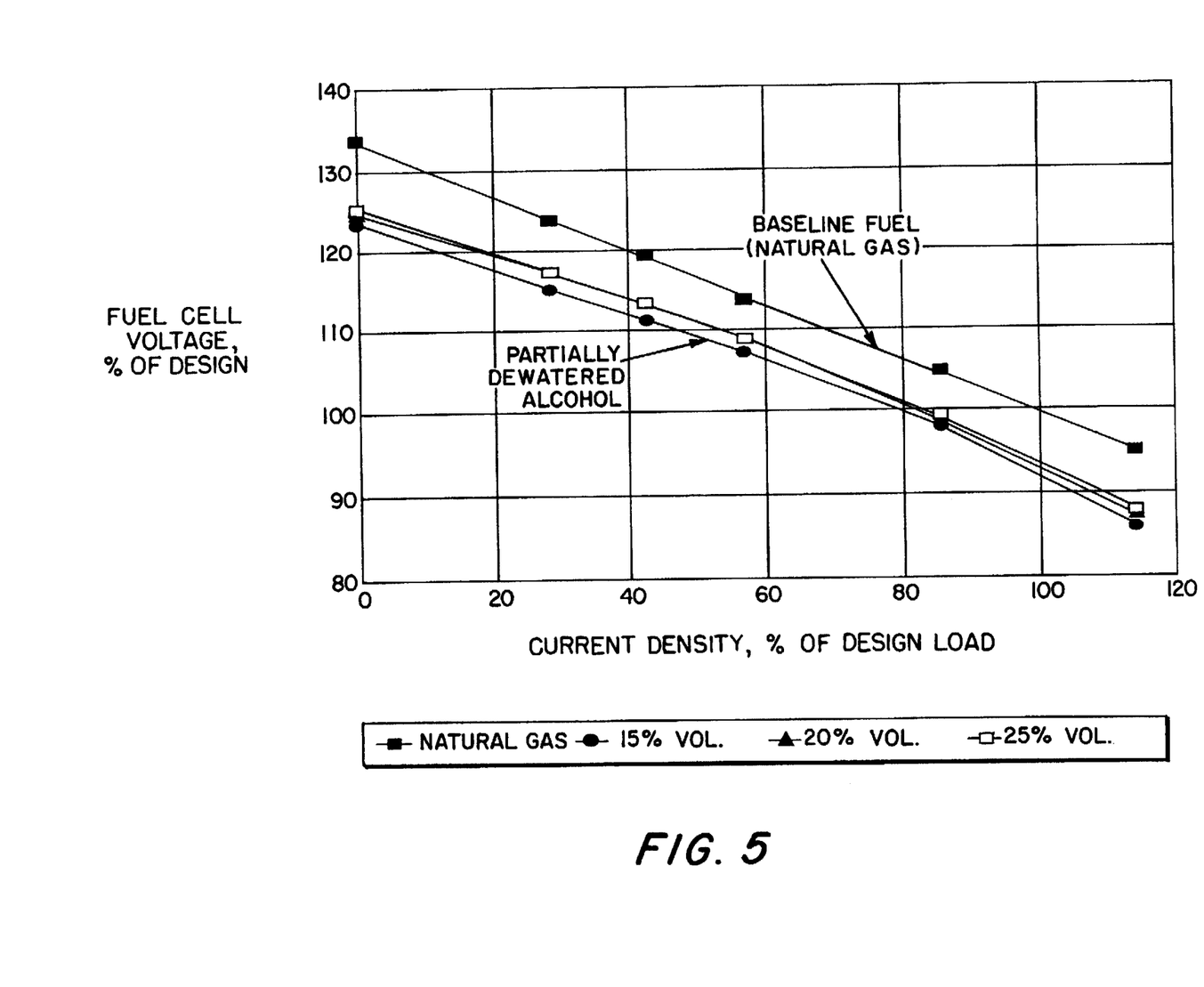
FIG. 5 is a graph of fuel cell performance.
Figure 6:
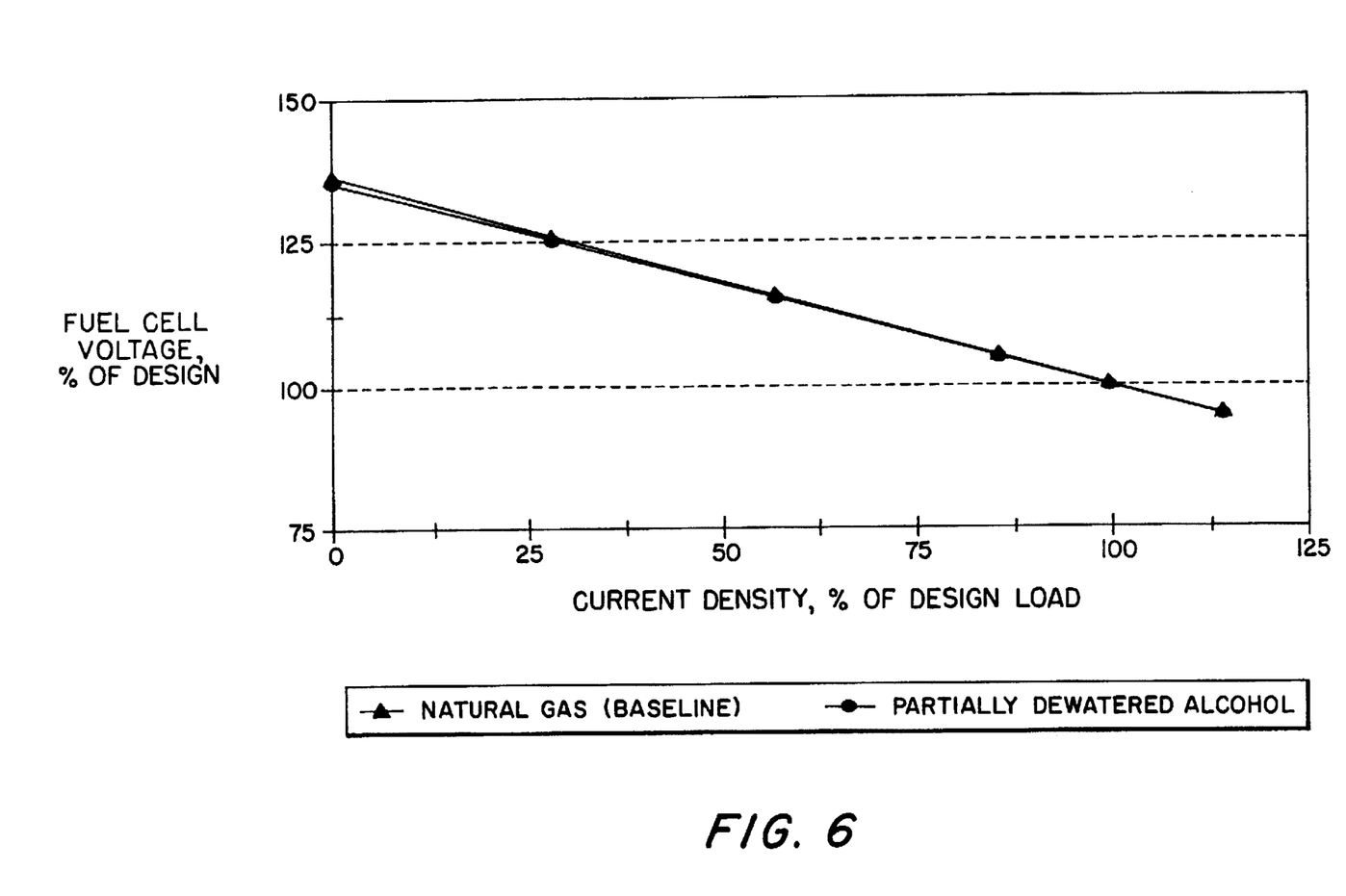
FIG. 6 is a graph of fuel cell performance.
Figure 7:
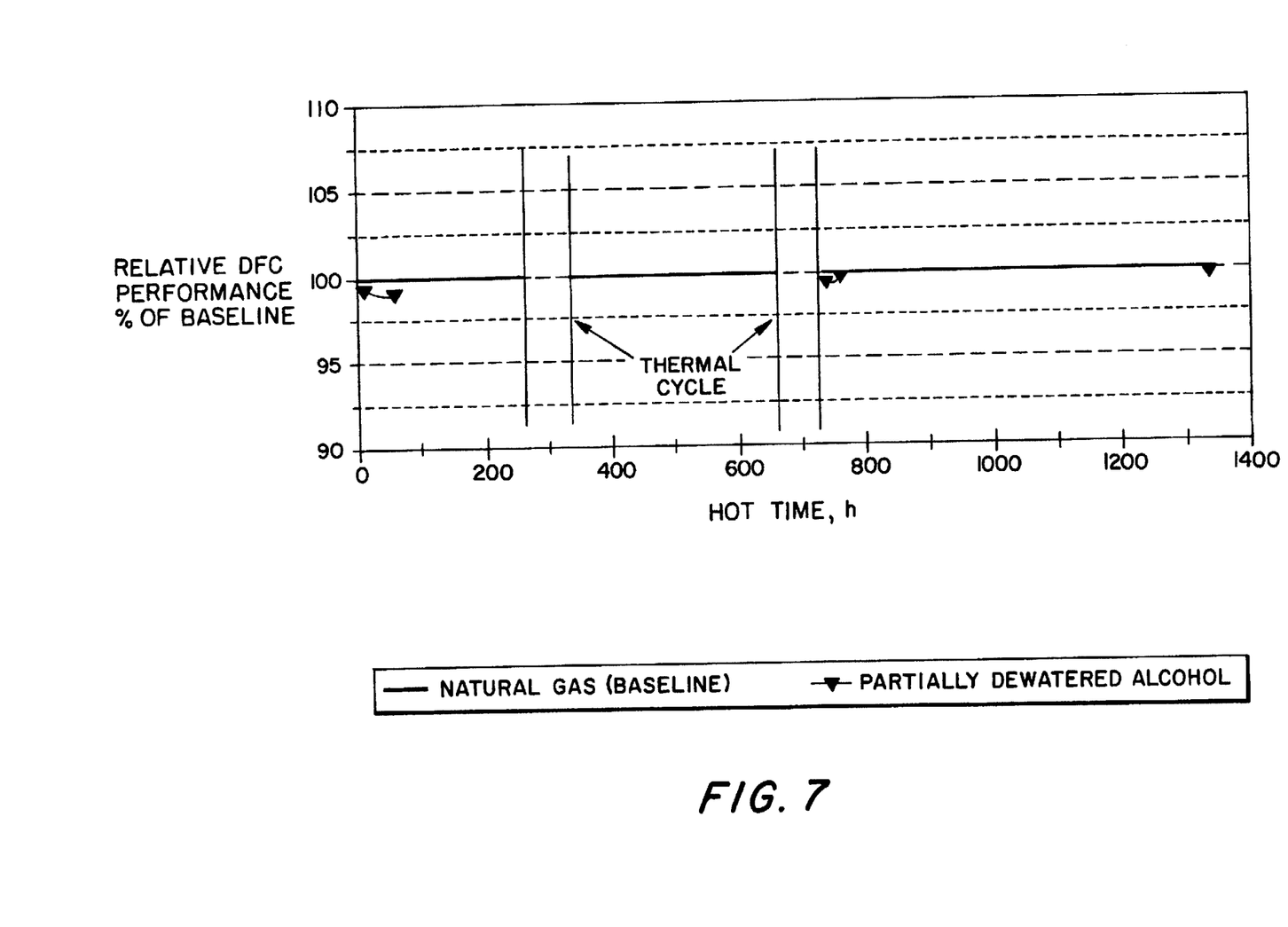
FIG. 7 is a graph of fuel cell performance.

FIGS. 5, 6, and 7 represent tests of partially dewatered alcohol fueling of fuel cells.

FIG. 5 shows that there is little difference in internally reforming fuel cell performance between 15% to 25% ethanol by volume, and only slight reduction in performance from that produced from fueling the DFC with natural gas (methane).

FIG. 6 shows that there is almost equivalent performance between fueling as DFC with natural gas and with fueling it with alcohol at 25% volume concentration through a preconverter.

FIG. 7 shows that fueling the DFC with 25% alcohol through a preconverter provided a performance almost equal to fueling with natural gas, with stable output for 1,400 hours.

Figure 8:
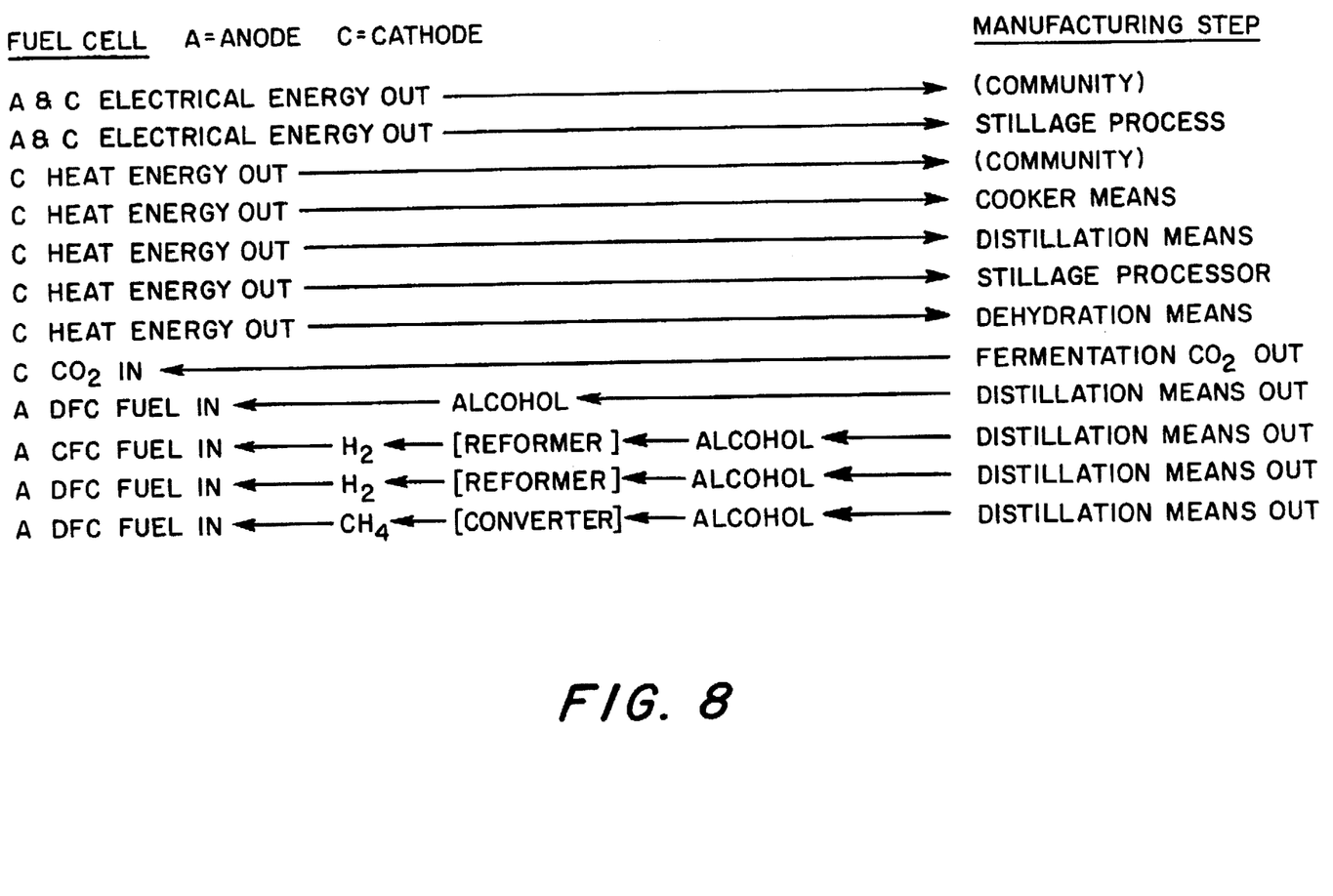
FIG. 8 is a schematic diagram of some of the interactions within the invention.

FIG. 8 summarizes for the convenience of the reader some of the interactions within the present invention.

Figure 9:
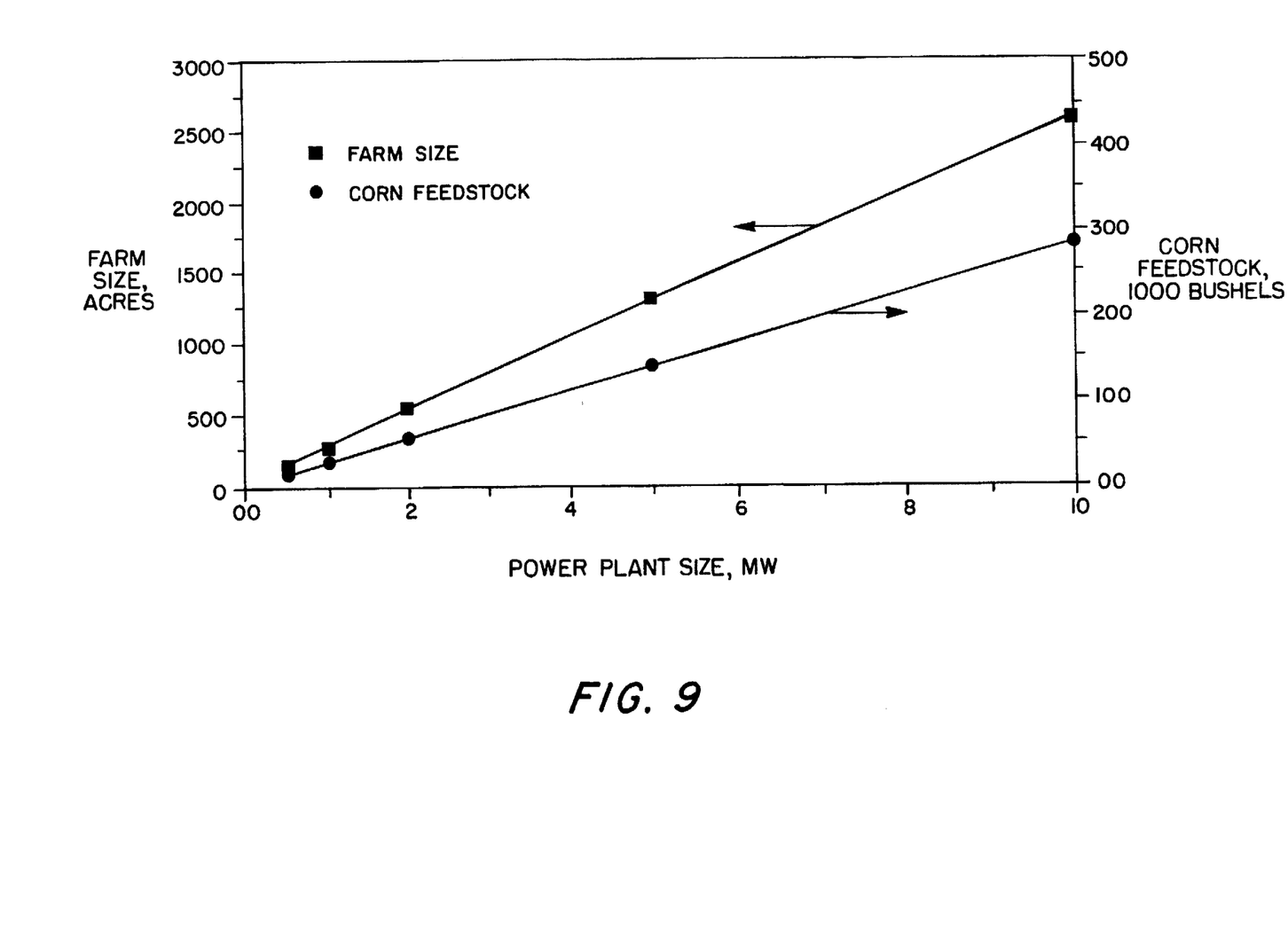
FIG. 9 is a graph of power plant size for various farm sizes.

FIG. 9 shows the expected electrical power that it is calculated to be obtainable from a cogeneration plant according to the present invention, for various size farms. This is based on 100 bushels/acre of corn yield, 2.6 gallons of alcohol per bushel of corn, and fuel cell efficiency of 50% A 500 acre farm can produce approximately 2 MW of electricity.

Figure 10:
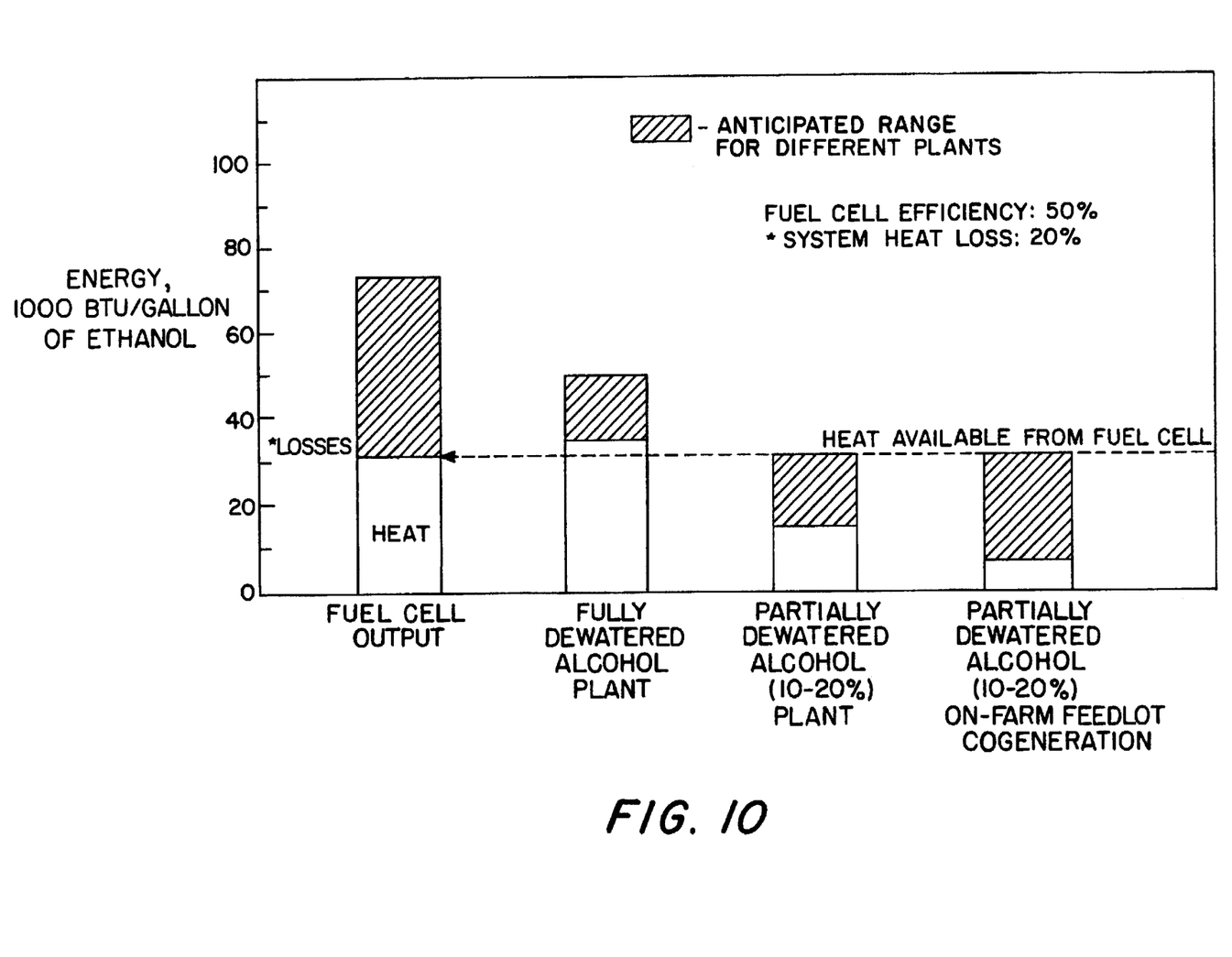
FIG. 10 is a graph of electricity and heat for community use provided by cogeneration.

FIG. 10 shows heat and electricity calculated to be available for community use from a cogeneration system of the present invention. (a) is energy at 1,000 BTU/gallons of ethanol, required for dewatering of the ethanol used to fuel the fuel cell. (b) is surplus electricity available for community use. (c) is surplus heat energy available for community use.

The fuel cell suitable for the present invention is not limited to a molten carbonate fuel cell. Any fuel cell fueled from partially dewatered alcohol, such as by taking the partially dewatered alcohol directly or comprising means converting the partially dewatered alcohol for use in the cell may be used. A cell that can use the by-product of fermentation, carbon dioxide, in the generation of energy is also suitable for making the present invention.

Although the present invention has been described with respect to details of certain embodiments thereof, it is not intended that such details be limitations upon the scope of the invention. It will be obvious to those skilled in the art that various modifications and substitutions may be made without departing from the spirit and scope of the invention as set forth in the following claims.

What is claimed is:

1. A biomass fermentation-electrical fuel cell cogeneration process including the steps of:
   (a) fermenting a biomass,
   (b) collecting carbon dioxide from the fermenting biomass,
   (c) delivering the carbon dioxide to the cathode of an electrical fuel cell which uses the carbon dioxide as a chemical reducing agent in generating electrical energy.

2. The process described in claim 1, further including transferring chemical heat generated by the electrical fuel cell's chemical process, to elements of the biomass.

3. The process described in claim 1, further including the steps of (d) collecting alcohol from the biomass fermented in step (a), and (e) fueling the anode of the electrical fuel cell with the alcohol obtained in step (d).

4. The process described in claim 3, further including transferring chemical heat generated by the electrical fuel cell's chemical process, to elements of the biomass.

5. The process described in claim 4 wherein the transferring of the heat includes applying the heat to fermented elements of the biomass, the heat being applied so that the heat causes alcohol to be driven from said fermented elements for said collecting of step (d) for use in step (e) fueling of the anode.

6. The process described in claim 4 further including steps (f) of cooking the biomass, and then (g) of saccharification of the cooked biomass, wherein the transferring of the heat includes the heat being applied to the biomass during step (f).

7. The process described in claim 1 further including applying electrical energy generated by the fuel cell to breaking the biomass into smaller parts so that it is in better condition for carrying out step (a).

8. A biomass fermentation-electrical fuel cell cogeneration process including the steps of:
   taking biomass, and
   (a) fermenting the biomass,
   (b) collecting alcohol of a preselected concentration from the biomass fermented in step (a)
   (c) fueling an electrical fuel cell with the alcohol obtained in step (b).

9. The process described in claim 8, further including the step of (d) transferring chemical heat generated by the electrical fuel cell's chemical process to elements of the biomass.

10. The process described in claim 9 wherein the transferring of the heat in step (d) includes applying the heat to fermented elements Of the biomass, the heat being applied so that the heat causes alcohol to be driven from said fermented elements for said collecting of step (b), for use in step (c) fueling of the anode.

11. The process described in claim 9, further including steps (e) of cooking the biomass, and then (f) of saccharification of the cooked biomass, wherein the transferring of the heat to elements of the biomass includes the heat being applied during step (e).

12. The process described in claim 9, wherein step (c) comprises step (g) of reforming the alcohol of step (c) at the anode of an internally reforming molten carbonate fuel cell.

13. The process described in claim 9, where step (c) comprises step (h) of reforming the alcohol of step (b) to provide hydrogen, and fueling the anode of a molten carbonate fuel cell with the hydrogen.

14. The process described in claim 9, wherein step (c) comprises the steps of (i) preconverting the alcohol of step (b) to provide methane, and then (j) reforming the methane at the anode of an internally reforming molten carbonate fuel cell.

15. The process described in claim 8, wherein step (c) comprises step (g) of reforming the alcohol of step (c) at the anode of an internally reforming molten carbonate fuel cell.

16. The process described in claim 8, where step (c) comprises step (h) of reforming the alcohol of step (b) to provide hydrogen, and fueling the anode of a molten carbonate fuel cell with the hydrogen.

17. The process described in claim 8, wherein step (c) comprises the steps of (i) preconverting the alcohol of step (b) to provide methane, and then (j) reforming the methane at the anode of an internally reforming molten carbonate fuel cell.

18. The process described in claim 8, wherein the fueling of step (c) consists of fueling predominantly with partially dewatered alcohol obtained from step (b).

19. The process described in claim 8 wherein said preselected concentration of alcohol is in a range of 1–60%.

20. The process described in claim 19, wherein said preselected concentration is in a range of 15–30%.

21. A process of fueling a molten carbonate fuel cell with a fuel that consists predominantly of partially dewatered alcohol of a preselected concentration.

22. The process described in claim 21 in which the fueling with the partially dewatered alcohol comprises reforming the partially dewatered alcohol to provide hydrogen and delivering the hydrogen to the anode of the fuel cell.

23. The process described in claim 21 in which the fueling with the partially dewatered alcohol comprises preconverting the alcohol to provide methane, and then reforming the methane at the anode of an internally reforming molten carbonate fuel cell.

24. The process described in claim 21 wherein said preselected concentration of alcohol is in a range of 1–60%.

25. The process described in claim 24 wherein said preselected concentration of alcohol is in a range of 15–30%.

26. A biomass fermentation-electrical fuel cell cogeneration system comprising:
   means for holding a biomass,
   means for fermenting the biomass, connected to said means for holding,
   means for separating alcohol of preselected concentration from the fermented biomass, connected to said means for fermenting, an electrical fuel cell connected to said means for separating alcohol from the fermented biomass, for receiving said alcohol for generating electrical energy electrochemically and chemical heat energy from said alcohol.

27. The cogeneration system described in claim 26, further comprising:

means for transferring heat energy, connected to said fuel cell and to said means for holding, for heating of said biomass.

28. The cogeneration system described in claim 27, further comprising:

said means for separating comprising distillation means, said means for transferring heat energy being connected to said distillation means for transferring the heat to said distillation means.

29. The cogeneration system described in claim 27, further comprising:

means for cooking said biomass, connected to said means for holding, said means for transferring heat energy being connected to said means for cooking.

30. The cogeneration system described in claim 27, further comprising:

means for receiving the biomass, connected to said means for holding the biomass, means for reducing the biomass to smaller parts, connected to said means for holding, between said means for receiving and said means for fermenting, and being connected to said electrical fuel cell for receiving electrical energy from said electrical fuel cell for operating said means for reducing.

31. The cogeneration system described in claim 27, further comprising:

means for collecting carbon dioxide from said means from fermenting, said electrical fuel cell further being connected to said means for collecting carbon dioxide for receiving the carbon dioxide for using the carbon dioxide chemically in said generating of electrical and heat energy.

32. The cogeneration system described in claim 27, further comprising:

means for trying the biomass, connected to said means for fermenting, said means for transferring heat energy being connected to said means for drying.

33. The cogeneration system described in claim 27, further comprising:

an anode exhaust converter connected between an anode and a cathode of said electrical fuel cell, and connected to said means for transferring heat energy.

34. The cogeneration system described in claim 26, further comprising:

means for collecting carbon dioxide from said means from fermenting, said electrical fuel cell further being connected to said means for collecting carbon dioxide for receiving the carbon dioxide for using the carbon dioxide chemically in said generating of electrical and heat energy.

35. The cogeneration system described in claim 26, further comprising:

means for reforming alcohol to hydrogen, connected to said means for separating and said fuel cell for reforming said alcohol to hydrogen for said receiving of said alcohol by said fuel cell.

36. The cogeneration system described in claim 26, further comprising:

means for converting alcohol to methane, connected to said means for separating and said fuel cell for converting said alcohol to methane for said receiving of said alcohol by said fuel cell.

37. The cogeneration system described in claim 26 wherein said preselected concentration of alcohol is in a range of 1–60%.

38. The cogeneration system described in claim 37 wherein said preselected concentration of alcohol is in a range of 15–30%.

39. A biomass-electrical fuel cell cogeneration system comprising means for making alcohol of preselected concentration from biomass and at least one of electrical energy and heat energy, by fermentation; electrical fuel cell means connected to said means for making alcohol for receiving said alcohol and generating electricity electrochemically and chemical heat energy from said alcohol, said means for making alcohol receiving said at least one of electrical energy and heat energy from said electrical fuel cell means.

40. The cogeneration system described in claim 39, further comprising:

means for reforming alcohol to hydrogen, connected to said means for making alcohol and to said fuel cell for reforming said alcohol to hydrogen for said receiving of said alcohol by said fuel cell for said generating of electricity and heat energy.

41. The cogeneration system described in claim 39, further comprising:

means for converting alcohol to methane, connected to said means for making alcohol and to said fuel cell, for converting said alcohol to methane for said receiving of said alcohol by said fuel cell for said generating of said electricity and heat energy.

42. The cogeneration system described in claim 39 wherein said preselected concentration of alcohol is in a range of 1–60%.

43. The cogeneration system described in claim 42 wherein said preselected concentration of alcohol is in a range of 15–30%.

44. A biomass-electrical fuel cell cogeneration system comprising means for making alcohol of preselected concentration from biomass and at least one of electrical energy and heat energy, by fermentation; electrical fuel cell means connected to said means for making alcohol for receiving said alcohol partially dewatered and generating electricity electrochemically and chemical heat energy from said partially dewatered alcohol, said means for making alcohol receiving said at least one of electrical energy and heat energy from said electrical fuel cell means.

45. The cogeneration system described in claim 44 wherein said preselected concentration of alcohol is in a range of 1–60%.

46. The cogeneration system described in claim 45 wherein said preselected concentration is in a range of 15–30%.

* * * * *

UNITED STATES PATENT AND TRADEMARK OFFICE
CERTIFICATE OF CORRECTION

PATENT NO. : 5,736,026
DATED : April 7, 1998
INVENTOR(S) : Patel et al.

It is certified that error appears in the above-identified patent and that said Letters Patent is hereby corrected as shown below:

Col. 2, line 2,   delete "thebiomass"   and insert   — the biomass —.

Col. 2, line 49,  delete "only-and"   and insert   — only and —.

Col. 3, line 6,   delete "sacharification"   and insert   — saccharification —.

Col. 4, line 16,  delete "Of"   and insert   — of —.

Col. 5, line 65,  delete "$H_2 \frac{1}{2} O_2$"   and insert   — $H_2 + \frac{1}{2} O_2$ —.

Col. 6, line 2,   delete "work.well"   and insert   — work well —.

Col. 8, line 3,   delete "Of"   and insert   — of —.

Col. 8, line 9,   delete "cocked"   and insert   — cooked —.

Col. 9, line 45,  delete "trying" and insert   — drying —.

Signed and Sealed this

First Day of September, 1998

BRUCE LEHMAN

Attest:

Attesting Officer

Commissioner of Patents and Trademarks